(12) United States Patent
Smith et al.

(10) Patent No.: US 6,355,252 B1
(45) Date of Patent: Mar. 12, 2002

(54) SOLUBLE VACCINIA VIRUS PROTEIN THAT BINDS CHEMOKINES

(75) Inventors: Geoffrey Smith, Oxford (GB); Aylwin Ng, Singapore (SG)

(73) Assignee: Isis Innovation Ltd., Oxford (GB)

( * ) Notice: Subject to any disclaimer, the term of this patent is extended or adjusted under 35 U.S.C. 154(b) by 0 days.

(21) Appl. No.: 09/367,781

(22) PCT Filed: Feb. 23, 1998

(86) PCT No.: PCT/GB98/00569

§ 371 Date: Nov. 22, 1999

§ 102(e) Date: Nov. 22, 1999

(87) PCT Pub. No.: WO98/37217

PCT Pub. Date: Aug. 27, 1998

(30) Foreign Application Priority Data

Feb. 21, 1997 (GB) ............................................... 9703592
Jan. 5, 1998 (GB) ............................................... 9800113

(51) Int. Cl.[7] ............................................. A61K 39/275
(52) U.S. Cl. ................................ 424/232.1; 424/205.1; 435/235.1; 435/236; 935/32
(58) Field of Search ............................... 424/199.1, 205, 424/205.1, 224.1, 227.1, 230.1, 231.1, 232.1, 239, 265.1, 268.1, 272.1; 435/69.1, 69.3, 172.3, 235.1, 236, 240, 320.1; 935/32, 65, 70

(56) References Cited

FOREIGN PATENT DOCUMENTS

WO          9633730       10/1996  .......... A61K/38/16

OTHER PUBLICATIONS

Nikolaevich et al. Two types of deletions in Orthopoxvirus genomes. Virus Genes. vol. 9, No. 3 (1995) pp. 231–245.*

Jackson et al. Expression of mouse interleukin–4 by a recombinant ectomelia virus suppresses cytolytic lymphocyte responses and overcomes genetic resistance to mousempox. Journal of Virology. vol. 75, No. 3 (2001) pp. 1205–1210.*

Virology; vol. 180; Howard et al.; "Vaccinia Virus Homologues of the Shope Fibroma Virus Inverted Terminal Repeat Proteins and a Discontinous ORF Related to the Tumor Necrosis Factor Receptor Family"; Jan. 1991; pp. 633–647.

Current Opinion In Immunology; vol. 8; No. 4; Geoffrey L. Smith; "Virus Proteins That Bind Cytokines, Chemokines or Interferons"; Aug. 1996; pp. 467–471

Journal Of Experimental Medicine; vol. 184; No. 3; Loetscher et al.; "Chemokine receptor specific for IP10 and MIG: Structure, Function, and Expression in Activated T–lymphocytes"; Sep. 1996; pp. 963–969.

* cited by examiner

Primary Examiner—Jeffrey Stucker
Assistant Examiner—Ulrike Winkler
(74) Attorney, Agent, or Firm—Volpe and Koenig, P.C.

(57) ABSTRACT

Use for novel chemokine-binding protein designated A41L, and chemokine-binding fragments thereof, for the treatment of conditions such as inflammation. The A41L protein beinds to chemokines in the CXC group.

3 Claims, 9 Drawing Sheets

CXC CHEMOKINES

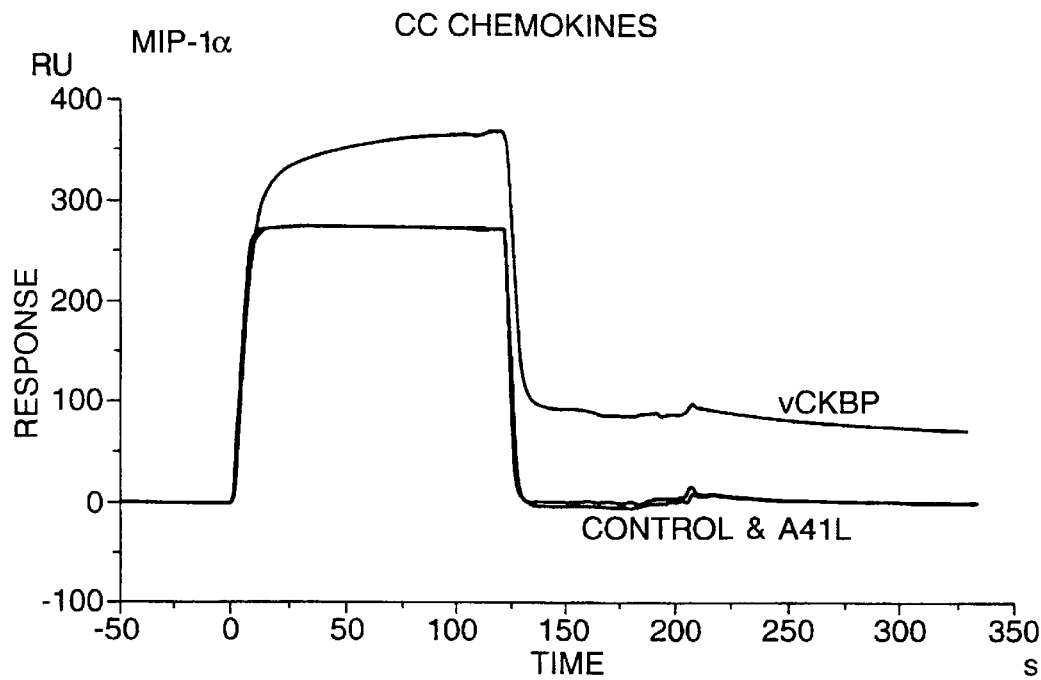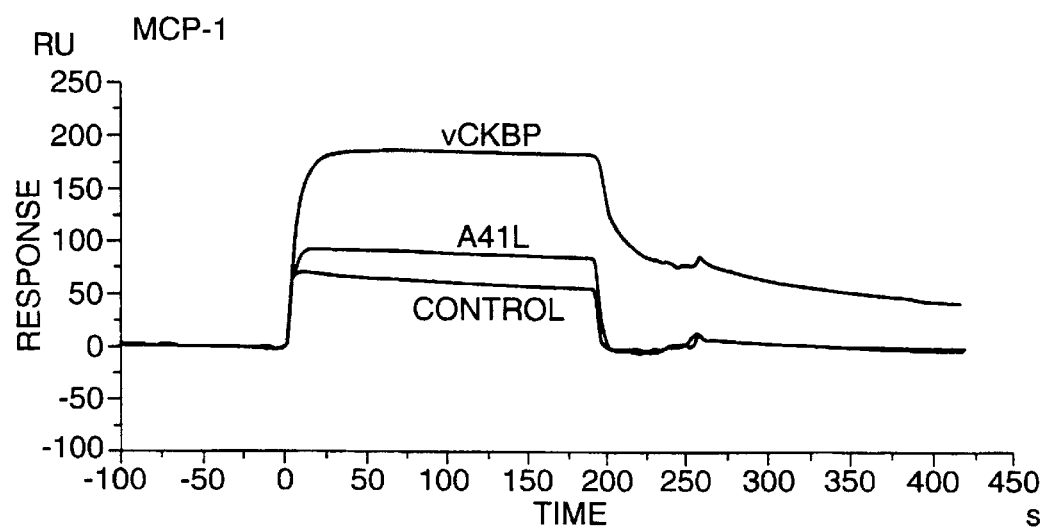

Fig.8.

```
  1  AAACTTGACA TTAGCATTTT ATTCTTATTA CAAAATATAA AATAAAATAT
 51  ACAATCCAAT ACTCACATAA TCCAACTCAC TCGAACACTA TTTTTCCAAT
101  TACGATAACA ATATTGCAGA ATGTACTCGT TAGTATTTGT TATTTTGATG
151  TGTATACCAT TTAGTTTTCA AACAGTGTAT GATGATAAAT CGGTATGCGA
201  TTCTGACAAT AAAGAATATA TGGGAATAGA AGTTTATGTA GAAGCAACGC
251  TAGACGAACC CCTCAGACAA ACAACGTGTG AATCCAAAAT CCATAAATAT
301  GGTGCATCTG TATCAAACGG AGGATTAAAT ATTTCTGTTG ATCTATTAAA
351  CTGTTTTCTT AATTTTCATA CAGTTGGTGT ATACACTAAT CGCGATACCG
401  TATACGCGAA GTTTGCTAGT TTGGATCCAT GGACTACGGA ACCTATAAAT
451  TCTATGACCC ATGACGATCT AGTAAAATTA ACAGAAGAAT GTATAGTGGA
501  CATTTATTTA AAATGTGAAG TGGATAAAAC AAAGGATTTC ATGAAAACTA
551  ACGGTAATAG ATTAAAACCA AGAGACTTTA AAACTGTTCC TCCTTCTAAT
601  GTAGGAAGCA TGATAGAACT ACAGTCTGAC TATTGCGTAA ACGATGTGAC
651  TACATACGTC AAAATATACG ATGAGTGTGG AAACATTAAA CAGCATTCCA
701  TTCCAACACT AAGAGATTAT TTTACCACCA AGAATGGTCA ACCACGTAAA
751  ATATTAAAGA AAAATTTGA TAATTGTTAA TTGTTATTTT TATAAAAACA
801  AGAACGGTAC GGCGATATTT ATTTTTTTCT AAAACATCTA ACCGAAGTAG
851  TGGTATGATA AAAATGTAGT GTAATTGTTA TATAGTGTAA CACGAAT
```

SOLUBLE VACCINIA VIRUS PROTEIN THAT BINDS CHEMOKINES

This invention relates to a novel chemokine-binding protein and chemokine-binding fragments thereof. In particular, the invention relates to uses of the protein or fragments in a medicament, for example as an anti-viral or an anti-inflammatory agent; and to methods for the detection and inhibition of chemokines.

Chemokines are a family of small secreted polypeptides that regulate trafficking and effector functions of leukocytes, and play an important role in inflammation and host defence against pathogens (D'Souza & Harden, 1996; Fauci, 1996; Howard et al., 1996; Murphy, 1996; Premack & Schall, 1996; Baggiolini et al., 1997). More than 30 chemokines have been identified and these are divided into at least three structural groups based on the number and arrangement of conserved cysteines: CC (β) chemokines such as RANTES (for regulation-upon-activation, normal T cell expressed and secreted) and macrophage inflammatory protein (MIP)-1α, CXC (α) chemokines such as interleukin-8 (IL-8) and growth-related oncogene (GRO)-α, and the C chemokine lymphotactin. The different chemokines have evolved to function with particular cell types: many CC chemokines are chemoattractants for monocytes or thymocytes, while many but not all CXC chemokines are chemoattractants for neutrophils. However, there is no rule relating chemokine structure and cellular specificity to other leukocyte subtypes. For example, the C chemokine lymphotactin is selective for T cells, the CC chemokine eotaxin is specific for eosinophils and the CXC chemokines IFN-γ-induced protein (IP-10) and monokine induced by IFN-γ (Mig) attract activated T cells.

Chemokine receptors (CKRs) are seven transmembrane domain proteins and are coupled to G proteins for signal transduction. Most CXC chemokines have high affinity for only a single CKR (IL-8 is an exception in binding to CXCR1 and CXCR2), whereas most CC chemokines bind to more than one CKR (Baggiolini et al., 1997).

The activity of chemokines is tightly regulated to prevent excessive inflammation that can cause disease. Inhibition of chemokines by neutralising antibodies in animal models (Sekido et al., 1993) or disruption of mouse chemokine genes (Cook et al., 1995) have confirmed a critical role of chemokines in vivo in inflammation mediated by virus infection or other processes. The production of soluble versions of cytokine receptors containing only the extracellular binding domain, represents a physiological and therapeutic strategy to blockade the activity of some cytokines (Rose-John & Heinrich, 1994). However, the seven transmembrane domain structure of CKRs makes the construction of soluble, inhibitory CKRs difficult, and thus mutated chemokine antagonists, blocking peptides or antibodies are alternative inhibitors of chemokines under evaluation (D'Souza & Harden, 1996; Howard et al., 1996).

CKRs play a critical role in transmission and dissemination of HIV by acting as a cofactor which is required together with CD4 for virus entry and infection (D'Souza & Harden, 1996; Fauci, 1996). The CXCR4 CKR is a cofactor for T cell line-tropic HIV isolates, whereas the CCR5 (and CCR3) CKRs are involved in infection by macrophage-tropic HIV strains. The importance of CCR5 in vivo is supported by the finding that individuals who are homozygous for a mutant version of the CCR5 gene are resistant to HIV infection. Binding of chemokines or mutated chemokine antagonists to CKRs block HIV infection, illustrating the potential of the blockade of HIV-CKR interaction as a preventive and therapeutic strategy against HIV (D'Souza & Harden, 1996; Fauci, 1996).

Poxviruses are a group of large DNA viruses that replicate in the cytoplasm of the cell and encode many of their own enzymes for transcription and DNA replication (Moss, 1996). Vaccinia virus (VV) is the most intensively studied poxvirus and is famous as the live vaccine that was used to eradicate smallpox (Fenner et al., 1988). Since 1982 VV has also been widely used as an expression vector and in vaccine research (Moss, 1991). The genome of VV strain Copenhagen has been completely sequenced and contains approximately 200 genes (Goebel et al., 1990). Those near the centre of the genome are mostly highly conserved between poxviruses and many are essential for virus replication. In contrast, genes located towards either end of the genome are more variable between different viruses and are frequently nonessential for virus replication (Johnson et al., 1993). A subset of these non-essential virus genes are important for blocking specific components of the host immune system and many affect virus virulence. Thus VV and other poxviruses express proteins that are able to block the action of interferons, complement, cytokines, chemokines, inflammation and fever (Alcami & Smith, 1995a; McFadden et al., 1995; Smith, 1996; Spriggs, 1996; Smith et al., 1997c). Many of these proteins are secreted from the infected cell and bind to host factors in solution or at the cell surface. In many cases there is amino acid similarity between the virus protein and the extracellular ligand-binding domain of a cell surface receptor for a particular ligand. In these cases it seems likely that the virus gene has been derived from the host during evolution.

Soluble chemokine-binding proteins have been previously detected in poxviruses. Firstly, the myxoma virus T7 protein, which was first identified as a soluble IFN-γR (Upton et al., 1992), binds to a range of chemokines through the heparin-binding domain and affects the infiltration of cells into infected tissue (Mossman et al., 1996; Lalani et al., 1997). The protein is described in WO 96/33730, designated CBP-1. In contrast, the IFN-γR from orthopoxviruses such as VV does not bind chemokines. (Alcami et al., 1998). Secondly, it was demonstrated that VV strain Lister expresses a soluble 35 kDa protein that is secreted from infected cells and which binds many CC chemokines (Graham et al., 1997; Smith et al., 1997a; Smith et al., 1997b; Alcami et al., 1998), but not CXC chemokines, through a domain distinct from the heparin-binding domain (Smith et al., 1997a; Smith et al., 1997b; Alcami et al., 1998). This protein has been called vCKBP (Alcami et al., 1998). The protein is also described in WO 97/11714, as p35. Very similar proteins are made by some but not all VV strains, cowpox virus, the leporipoxviruses, Shope fibroma virus (SFV) and myxoma virus (called T1 protein), and by variola major viruses e.g. protein G5R in India-1967 (Shchelkunov et al., 1994). Another VV gene encodes a protein more distantly related to vCKBP. In VV strain Copenhagen this was called A41L (Goebel et al., 1990), and in VV strain WR it was originally named SalF4L (Howard et al., 1991) but renamed SalF3L (Smith et al., 1991). Hereafter it is referred to as A41L. The relatedness of A41L and SFV T1, including the co-alignment of 8 cysteine residues was noted (Howard et al., 1991). Howard et al., 1991 also noted a potential site for attachment of carbohydrate via an asparagine residue and a putative signal peptide that might translocate the protein across the endoplasmic reticulum membrane and out of the cell. Other authors claimed there was no similarity between A41L and the 35 kDa protein of VV Lister and SFV T1 protein (Martinez-Pomares et al., 1995). In all three strains of variola major virus that have been sequenced there is an open reading frame (ORF) with more than 95% amino acid identity to the VV WR A41L protein termed 16L in strain Harvey (Aguado et al., 1992), A44L in strain Bangladesh-1975 (Massung et al., 1994) and A46L in strain India-1967 (Shchelkunov et al., 1994).

The similarity of A41L to vCKBP suggested that the A41L protein might bind chemokines as for vCKBP (Alcami et al., 1998). However Alcami et al., (1998) reported the supernatants of cells infected with VV WR or VV Lister from which the gene encoding the 35 kDa protein had been deleted (Patel et al., 1990), did not contain a protein that could be crosslinked to MIP-1α, RANTES, IL-8 or GRO-α (Alcami et al., 1998).

It has now been discovered that gene A41L encodes a 30 kDa protein that is secreted from cells infected by all strains of orthopoxvirus examined including 16 strains of VV and 2 strains of cowpox virus. In addition it is predicted to be expressed from all 3 strains of variola major virus for which sequence data are available (Aguado et al., 1992; Massung et al., 1994; Shchelkunov, 1995). The protein contains O— and N-linked carbohydrate. A VV WR deletion mutant lacking the A41L gene was constructed and shown to replicate in cell culture to the same titre as wild type and revertant viruses. Using A41L protein made by recombinant baculovirus in surface plasmon resonance (BIAcore), the protein was found to bind the CXC chemokines Mig and IP-10, but not other CXC, CC or C chemokines.

The invention provides in one aspect a medicament comprising an effective amount of an A41L protein or a chemokine-binding fragment thereof, together with a pharmaceutically acceptable carrier.

The invention is concerned in particular with the use of an A41L protein or a chemokine-binding fragment thereof as an anti-inflammatory agent. The A41L protein and fragments will be useful for the treatment of conditions mediated by chemokines, in particular CXC chemokines and IFN-γ-induced chemokines such as Mig and IP-10.

The invention is also concerned with the use of an A41L protein or a chemokine-binding fragment as an anti-viral agent. The A41L protein or fragment will inhibit binding to and/or infection of a target cell by pathogens such as HIV which mediate infection of a target cell via a cellular chemokine receptor.

The medicaments described herein may be useful for treatment and/or prophylaxis.

In another aspect, the invention provides a recombinant poxvirus which is genetically engineered to be incapable of expressing a native A41L protein.

Preferably, the recombinant poxvirus is incapable of expressing a chemokine-binding A41L protein, for example by deletion of all or a substantial part of the A41L gene. The recombinant poxvirus may be for example a genetically engineered vaccinia virus. Vaccinia virus MVA, which is currently being developed for use in vaccines, is of particular interest in connection with this aspect of the invention. MVA genetically engineered so as to be incapable of expressing a chemokine-binding A41L protein has the anticipated advantages of being safer and less immunogenic than its counterpart expressing native A41L protein.

In a further aspect, the invention provides a detection method comprising the steps of:

a) providing a chemokine-binding molecule which is an A41L protein or a chemokine-binding fragment thereof;
b) contacting the chemokine-binding molecule with a sample;
c) detecting an interaction of the chemokine-binding molecule with a chemokine in the sample.

Thus, the invention may be used to detect the presence of one or more chemokines in a biological sample. The chemokine-binding molecule may be usefully immobilised on a solid support.

In another aspect, the invention provides a method for inhibiting the activity of one or more chemokines in a sample, which method comprises contacting the sample with an effective amount of a chemokine-binding molecule which is an A41L protein or a chemokine-binding fragment thereof.

In further aspects the invention provides a purified A41L protein or a chemokine-binding fragment thereof, for use in a method or a medicament as described herein; and a kit comprising such a purified A41L protein or fragment.

An amino acid sequence for the A41L protein is shown in FIG. 1. The sequence shown is for the VV WR A41L protein (accession no. D11079). Also shown for comparison is the amino acid sequence of vCKBP from VV Lister (DNA database of Japan, accession no. D00612).

The invention is concerned with A41L proteins (now also referred to as vCKBP-2) from poxviruses including vaccinia viruses and variola major viruses and from any other viral or non-viral source. Viral A41L proteins may be expected to have about 50% or more amino identity with the A41L amino acid sequence shown in FIG. 1, or particularly 80% or more, or 90% or more, or 95% or more amino acid identity with the A41L sequence in FIG. 1. Cellular homologues of the A41L protein which have the same or similar chemokine-binding capability may be expected to have a far lower amino acid identity with the sequence shown in FIG. 1, for example about 25%.

A41L proteins from different organisms may also be identified by the following shared characteristics:

- conserved cysteine residues in the amino acid sequence which form intramolecular disulphide bonds.
- chemokine-binding properties.
- a similar size.
- amino acid identity/similarity. Amino acid similarity means amino acid residues having similar properties such as charge and hydrophobicity; where one amino acid may be conservatively substituted (that is without significant effect on the structure of the protein) for another, there is "similarity" between the two.
- acidity; the proteins are all reasonably acidic. This ties in with their function since chemokines tend to be basic proteins. The isoelectric point of the A41L protein from W WR is 5.4.

The A41L proteins for use in the invention may be provided in native or in mutant form. Known methods, in particular genetic manipulation techniques, can be used to provide modified versions of the protein which have altered characteristics compared to the native protein. Desirable altered characteristics may be for example an altered binding capability to enhance binding to the chemokines.

The invention also envisages the use of fragments of the A41L protein, which fragments have chemokine-binding properties. The fragments may be peptides derived from the protein. Use of such peptides can be preferable to the use of an entire protein or a substantial part of a protein, for example because of the reduced immunogenicity of a peptide compared to a protein. Such peptides may be prepared by a variety of techniques including recombinant DNA techniques and synthetic chemical methods.

It will also be evident that the A41L proteins for use in the invention may be prepared in a variety of ways, in particular as recombinant proteins in a variety of expression systems.

Such expression systems include for example poxvirus or non-poxvirus expression systems. Any standard systems may be used such as baculovirus expression systems or mammalian cell line expression systems.

FIG. 1 shows an alignment of the VV WR A41L protein with vCKBP of VV Lister.

FIG. 8 shows the nucleotide sequence of the VV strain WR A41L gene and flanking sequences.

Figure 2:
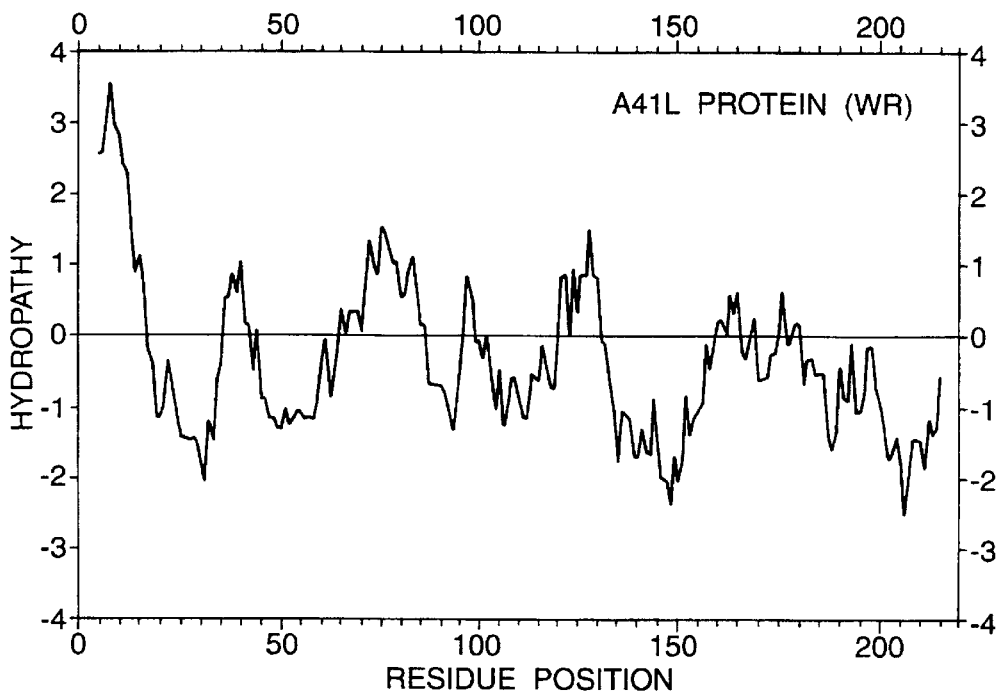
FIG. 2 shows hydropathy profiles for A41L from VV strain WR and vCKBP of VV strain Lister.
Figure 2:
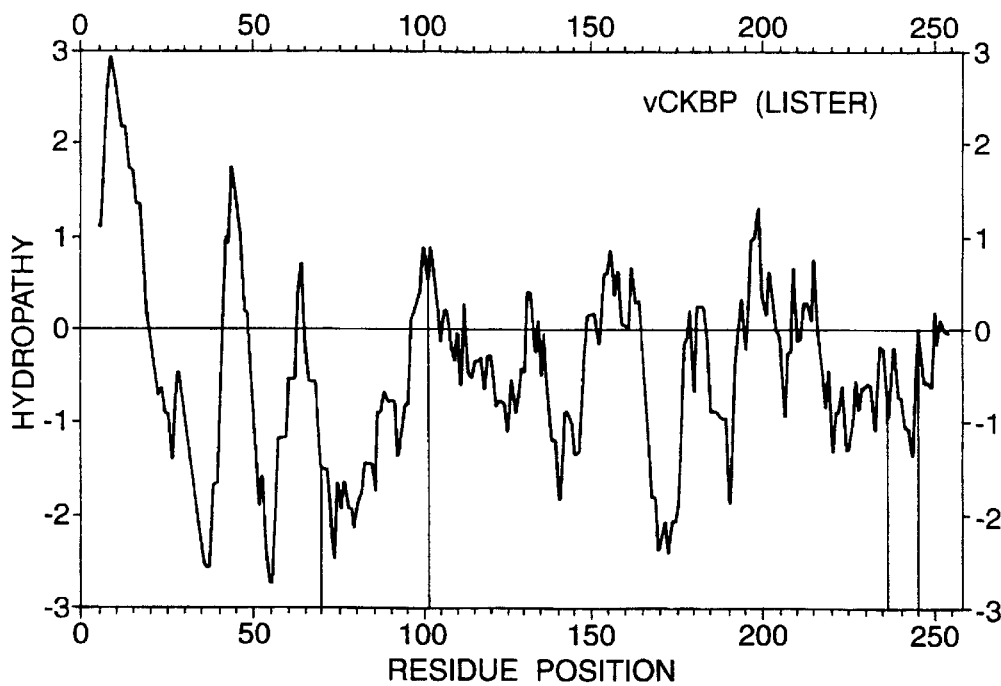

The invention will now be further described in the Examples which follow, which are intended to illustrate the invention and not to limit the scope of the invention in any way.

EXAMPLES

Materials and Methods

Cells and viruses

The orthopoxvirus strains used in this study are described elsewhere (Alcami & Smith 1995b; Alcami et al., 1998). The VV strain WR was grown in BS-C-1 cells in Dulbecco's modified Eagle's medium (DMEM) supplemented with 10% foetal bovine serum (FBS) and was titrated on these cells as described previously (Mackett et al., 1985). D980R and CV-1 cells were grown in DMEM containing 10% FBS.

Chemokines

Recombinant human chemokines IL-8, neutrophil activating protein (NAP)-2, GRO-α, platelet factor (PF) 4, stromal-derived factor (SDF)-1α, epithelial neutrophil activating protein (ENA)-78, Mig, IP-10, RANTES, MIP-1α, MCP-1, MCP-2, eotaxin and lymphotactin were purchased from PeproTech, GRO-γ and I-309 were purchased from R&D Systems, and the anaphylatoxin C5a was purchased from Sigma.

Construction of VV A41L deletion and revertant viruses

A plasmid suitable for the construction of a VV strain WR mutant lacking the A41L gene by transient dominant selection (Falkner & Moss, 1990) was assembled by polymerase chain reaction (PCR) and DNA cloning. Oligonucleotides that flanked the left or right side of the A41L gene were used to generate PCR products that contained terminal HindIII and BamHI (left flank) or BamHI and EcoRI (right flank) restriction enzyme sites. These PCR fragments were then digested at their termini with the appropriate restriction enzymes and cloned sequentially into plasmid pSJH7 cut with the same enzymes (Hughes et al., 1991) to form a plasmid pΔA41L. This plasmid lacked 90% of the A41L ORF (codons 1-201) and contained the Escherichia coli guanylphosphoribosyl transferase gene (Ecogpt) (Boyle & Coupar, 1988) under the control of the VV p7.5K promoter (Mackett & Smith, 1982) distal to the sequences surrounding the A41L gene. The fidelity of the sequence of the PCR-derived regions of the plasmid was confirmed by DNA sequencing using an Applied Biosystems Inc. 373 fluorescent automated DNA sequencer. Plasmid pΔA41L was then transfected into CV-1 cells that had been infected with VV strain WR at 0.05 plaque forming units (pfu)/cell. Two days later the virus present in the cells was harvested, diluted and used to infect monolayers of BS-C-1 cells in the presence of mycophenolic acid (MPA), xanthine and hypoxanthine as described (Falkner & Moss, 1988). Plaques formed in the presence of MPA represented viruses expressing Ecogpt due to integration of plasmid pΔA41L by a single crossover recombination event. After an additional plaque purification on BS-C-1 cells in the presence of MPA, MPA-resistant virus isolates were used to infect monolayers of d980R cells in the presence of 6-thioguanine (6-TG) as described (Kerr & Smith, 1991). Plaques formed represented virus isolates from which the Ecogpt cassette and plasmid sequences had been lost by recombination and were either wild type or A41L deletion mutant (ΔA41L). These were distinguished by PCR using oligonucleotides flanking the A41L gene. A plaque purified wild type virus (vA41L) and a deletion mutant (vΔA41L) derived from the same MPA-resistant intermediate virus were plaque purified twice more and then amplified and purified as described previously (Mackett et al., 1985).

A revertant virus in which the A41L gene was re-inserted into vΔA41L was constructed by transient dominant selection (Falkner & Moss, 1990) using plasmid pA41L. This plasmid contained the complete A41L gene and flanking sequences cloned between the SalI and EcoRI sites of plasmid pSJH7. pA41L was transfected into vΔA41L-infected CV-1 cells and MPA-resistant virus was isolated as described above. Such a virus was then plated onto d980R cells in the presence of 6-TG and 6-TG-resistant viruses were screened for a wild type A41L genotype by PCR (as above). After further plaque purification this virus was amplified, purified and called vA41L-rev.

Genome analysis of virus isolates

Viruses vA41L, vΔA41L and vA41L-rev were grown in BS-C-1 cells and DNA was extracted from purified virus cores as described previously (Esposito et al., 1981). These DNA samples were then analysed by PCR and Southern blotting (Southern, 1975). PCR analysis used oligonucleotides flanking the A41L locus to distinguish between wild type and mutant A41L alleles. For Southern blot analyses virus DNA was digested with EcoRV, electrophoresed on a 0.8% agarose gel and transferred to nylon filters (Hybond-N, Amersham). Filters were hybridised with fluorescein-labelled DNA probes derived from either within the region of A41L deleted from vΔA41L or from a region extending from the 5' end of the gene into the left flanking region. Bound probes were detected with peroxidase-conjugated anti-fluorescein antibodies and enhanced chemiluminescence (ECL) reagents (Amersham).

Expression and purification of A41L protein from recombinant baculovirus

The A41L ORF was amplified by PCR using oligonucleotides that introduced restriction enzyme sites HindIII and XhoI at the 5' and 3' of the ORF, respectively. The DNA fragment was digested with the same enzymes and cloned into HindIII and XhoI-cut pBAC-1 (R&D Systems) generating plasmid pAcA41Lhis so that the A41L ORF was downstream of the Autographa californica nuclear polyhedrosis virus (AcNPV) polyhedron gene promoter and linked to 6 histidine residues at the C terminus. Plasmid pAcA41Lhis was used to construct recombinant baculoviruses as described (Alcami & Smith 1992; Alcami et al., 1998). Spodoptera frugiperda (Sf)21 cells were cotransfected with purified linear AcNPV DNA (BacPAK6, Clontech) and pAcA41Lhis according to the manufacturer's instructions and recombinant virus AcA41Lhis was isolated. A high titre stock ($10^8$ pfu/ml) of AcA41Lhis was generated from the working stock and was used to infect Sf21 cells (seeded onto plastic flasks at $2 \times 10^5$ cells/cm$^2$) at 10 pfu/cell in TC100 medium with 10% FBS. After 3 h the virus inoculum was removed, the cells were washed and overlayed with serum-free TC100. After 60 h, the supernatant was collected, centrifuged at 2,000 rpm (GH-3.7 rotor in a Beckman GPR centrifuge) for 5 min at 4 C to remove cellular debris, filtered through a 0.2 $\mu$m filter (Nalgene) and then centrifuged at 20,000 rpm (SW28 rotor in a Beckman L8-M ultracentrifuge) for 30 min at 4 C to pellet virus particles. The supernatant was collected, dialysed against 20 mM Tris-HCl (pH 7.9) in 500 mM NaCl, and purified by Ni$^{2+}$ chelate affinity chromatography. Nitrilotriacetic acid (NTA) resin pre-charged with Ni$^{2+}$ (Qiagen) was equilibrated in binding buffer (20 mM Tris-HCl pH 7.9, 0.5 M NaCl, 5 mM imidazole), before being mixed with the supernatant. The slurry was rotated continuously for 3 h, washed with 50 ml of binding buffer followed by 50 ml of 20 mM imidazole in binding buffer and then poured into a column. The column was further washed (at a flow rate of 0.2 ml/min) with binding buffer containing increasing concentration of imidazole up to 50 mM, before eluting the bound A41Lhis protein with 120 mM imidazole. Aliquots of the fractions were analysed by sodium dodecyl sulphate-polyacrylamide gel electrophoresis (SDS-PAGE) (Laemmli, 1970) on 10% gels and visualised by staining with Coomassie blue. The fractions containing the eluted A41Lhis protein were pooled, dialysed into 50 mM Tris-HCl pH 7.0, 20 mM NaCl to remove imidazole and to prepare the sample for further purification and concentration by fast protein liquid chromatography (FPLC) using a mono-Q anion exchanger (Pharmacia). A41Lhis has a predicted isoelectric (pI) point of 5.4 and so readily bound to mono-Q at pH 7.0 and was eluted at 400 mM NaCl during washing of the column with a 10 ml gradient of 20 mM to 1 M NaCl. The protein concentration in fractions was determined by Bradford assay and by comparisons with known concentrations of BSA standards on SDS-PAGE.

Immunisation of rabbit to produce an A41L monospecific antibody

New Zealand white rabbits were injected intramuscularly with 80 $\mu$g of purified A41Lhis protein emulsified with an equal volume of Freund's complete adjuvant and boosted 3 times at 3 week intervals with 200 $\mu$g of the same antigen emulsified in Freund's incomplete adjuvant. Pre-immune and immune serum samples were taken prior to immunisation and 2 weeks after the final immunisation.

Immunoblotting

BS-C-1 cells were infected with the indicated orthopoxviruses at 10 pfu/cell for 1.5 h at 37 C, and after washing away unbound virus, the cells were incubated for 16 h in minimal essential medium (MEM) without serum. Supernatants from infected cells were then prepared as described previously (Alcami & Smith, 1995b). Alternatively, Sf21 cells were infected with AcNPV or AcA41Lhis at 10 pfu/cell and 3 days later the supernatants were harvested and clarified by centrifugation (2,000×g, 10 min at 4 C). All samples were resolved by SDS-PAGE on 10% gels. After electrophoretic transfer of proteins to nitrocellulose membranes (Towbin et al., 1979) the blots were incubated sequentially with rabbit anti-A41L serum (diluted 1:2000), a goat anti-rabbit peroxidase-conjugate, and ECL reagents (Amersham) as described previously (Parkinson & Smith, 1994) and as directed by the manufacturer.

Surface plasmon resonance (BIAcore analysis)

The carboxymethylated dextran surface of a BIAcore sensor chip CM5 was activated with 35 $\mu$l of 50 mM N-hydroxysuccinimide (NHS) and 200 mM N-ethyl-N'-(3-dimethylaminopropyl)carbodiimide hydrochloride (EDC) at a flow rate of 5 $\mu$l/min over the chip, through three of the four flow cells. Coupling of proteins onto the activated chip surface was achieved by passing 35 $\mu$l of purified, baculovirus-expressed A41Lhis (10 ng/$\mu$l) and 35Khis (10 ng/$\mu$l) (Alcami etal., 1998) in 15 mM acetate pH 4.0 through flowcells 3 and 4 respectively, at a flow rate of 5 $\mu$l/min. This was followed by passing 35 $\mu$l of 1 M ethanolamine hydrochloride-NaOH pH 8.5 at a flow rate of 5 $\mu$l/min through the three NHS/EDC-activated flowcells, to deactivate the chip surface. Various recombinant chemoattractant molecules (e.g. anaphylatoxin C5a, and chemokines from the CXC, CC and C families) were passed across a CM5 sensor chip surface at a concentration of 1 $\mu$M in HEPES buffered saline (HBS) (10 mM HEPES, 150 mM NaCl, 3 mM EDTA) containing 0.005% Tween-20, at a flow rate of 5 $\mu$l/min over flowcells with or without A41 His or 35KHis coupled to the chip surface. A positive interaction of the chemoattractant molecules (analyte) with the surface-coupled proteins (ligand) was indicated by an increase in the final base line (in response units) after the injected analyte had been eluted from the flowcells. After each injection of analyte, the sensor chip surface was regenerated with a 5 $\mu$l pulse of 0.1 M HCl at a flow rate of 5 $\mu$l/min, to strip the bound analyte off the ligand coupled to the chip surface, in order to prepare the chip surface for the next chemoattractant molecule to be injected.

Histological examination of VV-induced lesions in a rabbit skin model

VVs vA41L, vΔA41L and vA41L-rev were diluted in PBS and were injected sub-cutaneously with $10^4$, $10^5$ or $10^6$ pfu per site, along the left and right flanks of a female New Zealand White rabbit (weighing 1.5 kg) which was sacrificed 3 days post injection. The titres of the viruses used for infection were confirmed by plaque assays. Biopsy tissue samples from lesions which developed at the sites of injection, were frozen using O.C.T. Tissue-Tek (Bayer Diagnostics) in isopentane bath over dry ice for cryosectioning. The cryosections (10 $\mu$m thick) were placed on glass slides (Horwell Superfrost), fixed in 2% (w/v) paraformaldehyde on ice and subjected to membrane permeabilisation with 0.1% Triton-X 100 in PBS, quenching at 37 C for 5 mins to remove endogenous peroxidase using glucose oxidase (0.5 units/ml) in 0.1 M phosphate buffer (pH 7.4) containing 0.2% (w/v) glucose and 1 mM sodium azide, three washes (for mins) with PBS (containing 0.1% Triton), and blocking for 30 mins with 5% normal horse serum (Sigma). The sections were then either immunostained with mouse anti- rabbit CD43 antibody (Serotec) at 1:100 dilution in 5% normal horse serum (for 1 h) to detect infiltrating leukocytes (particularly T lymphocytes, monocytes and macrophages) or mouse anti-14 k monoclonal antibody (MAb 5B412F2) (Czerny & Mahnel, 1990) at 1:1000 dilution (for 1 h), for the presence of VV in the sections. The sections were washed (3 times) in PBS with 0.1% Triton, followed by incubation with 1:100-diluted biotinylated horse anti-mouse secondary antibody (Vector Laboratories) for 30 mins, washed as before and then treated for 30 mins with Vectastain Elite ABC Reagent (Vector Laboratories). After 2 washes for 5 mins, immunostained sections was visualised using the chromogenic substrate, diaminobenzidine tetrahydrochloride (DAB) (Sigma) at a concentration of 0.5 mg/ml in 10 mM imidazole, which produces a reddish brown precipitate, followed by 2 further washes (as above)

and another with PBS. The sections were counterstained with cresyl violet acetate (1%), dehydrated through increasing concentrations of 70%, 80%, 95%, and absolute ethanol, and mounted with coverslips using DPX (BDH Merck). Histological examination of these sections was done under bright field illumination using a Zeiss Axiophot photomicroscope.

Results

The A41L protein is related to the T1/35 kDa protein family

Figure 1:
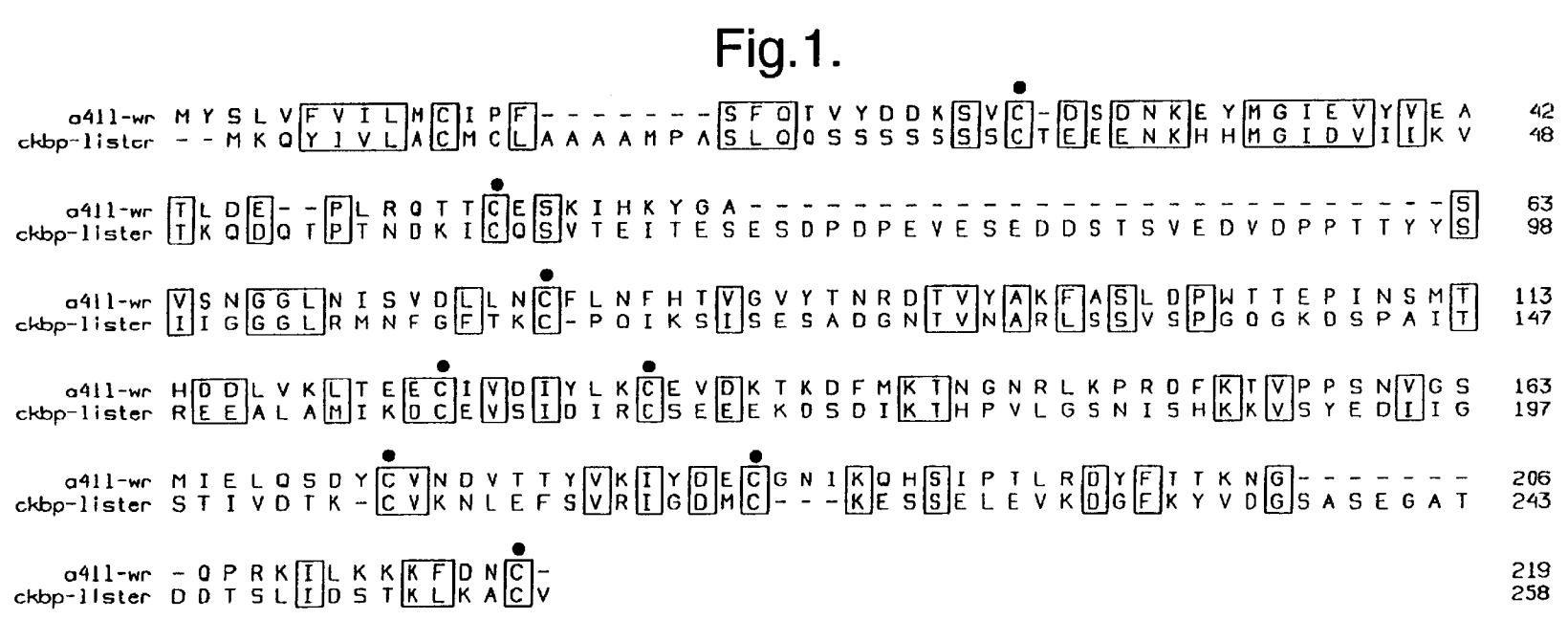

The A41L gene was predicted to encode a 25 kDa protein with a 219 amino acid residues (Goebel et al., 1990; Howard et al., 1991). Computational analyses had revealed this protein was related to SFV T1 protein (Howard et al., 1991). The A41L gene product also shares 25% amino acid identity with the recently described chemokine-binding protein, vCKBP, expressed by orthopoxviruses and various VV strains including Lister but not WR (Graham et al., 1997; Smith et al., 1997a; Alcami et a., 1998). This similarity is illustrated further in FIG. 1 by the alignment of the VV WR A41L protein with vCKBP of VV Lister (Patel et al., 1990). A41L is also related to the G5R protein from variola virus strain Bangladesh-1975(Massung et al., 1994) and the SFV T1 protein (Upton et al., 1987). The A41L protein of VV strain WR shares 97.7% amino acid identity with the A41L protein of VV strain Copenhagen (Goebel et al., 1990), and 96.3% identity with the 16L protein of variola virus strain Harvey (Aguado et al., 1992), and similar degrees of relatedness with protein A44L from variola virus strain Bangladesh-1975(Massung et al., 1994) and protein A46L from variola virus strain India-1967 (Shchelkunov et al., 1994). Note the conservation of eight cysteine residues and the similar length of these proteins. Both the A41L gene product and vCKBP do not have significant similarities with other non-viral protein sequences in databases. The relationship between the VV A41L protein and vCKBP is also illustrated by the similar hydropathy profiles of the two proteins (FIG. 2) and their acidic nature, pI 5.4 for A41L and 4.3 for vCKBP.

The A41L gene is non-essential for virus replication in cell culture

Sequence analysis of the genomes of variola virus strains Harvey, India-1967 and Bangladesh-1975and VV strains Copenhagen and WR showed that a protein equivalent to VV WR A41L protein is present in each virus and is highly conserved. This suggested that the protein might have an important function for the virus. To explore this further we attempted to make a VV deletion mutant lacking the A41L gene. Because the A41L protein is related to VCKBP of VV Lister and some other VV strains (Alcami et al., 1998) it was possible that vCKBP might compensate functionally for loss of the A41L gene. To avoid this possible complication, VV strain WR was selected because it does not express vCKBP. Despite the conservation of A41L, a viable deletion mutant was isolated.

Figure 3:
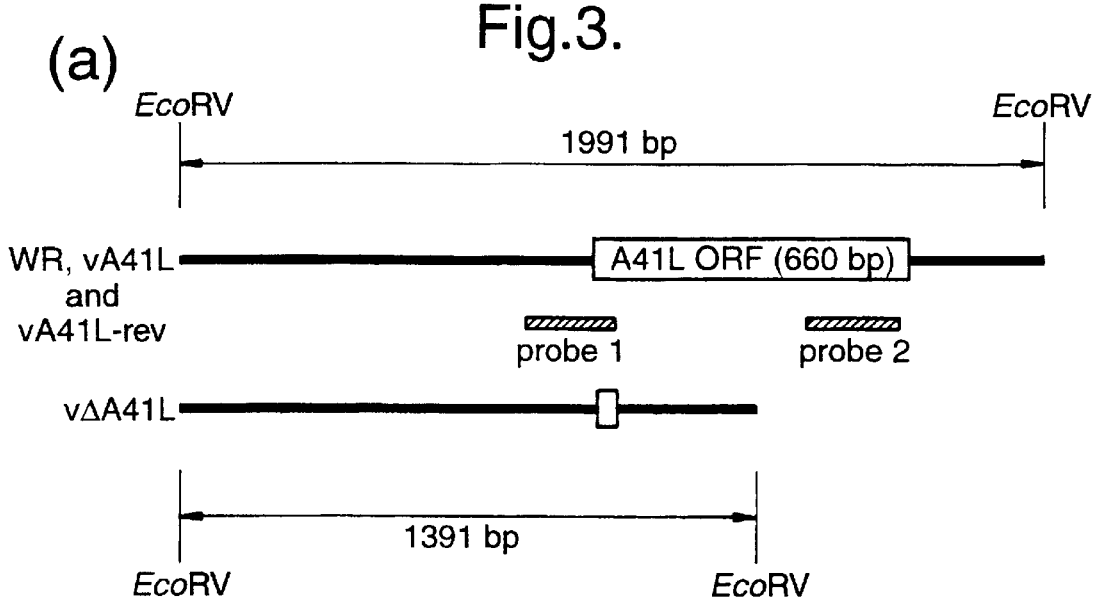
FIG. 3 shows analysis of vΔA41L and wild type and revertant viruses.
Figure 3:
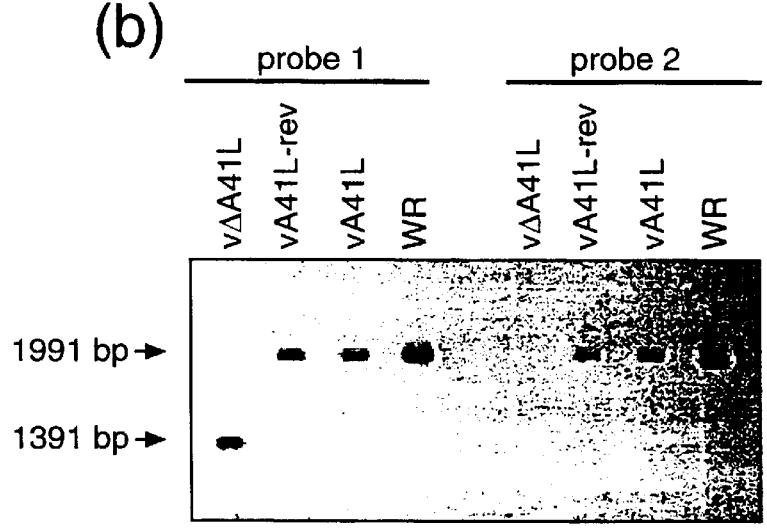

Analysis of the genomes of vΔA41L and wild type (vA41L) and revertant (vA41L-rev) viruses indicated that they had the predicted genome structures (FIG. 3). EcoRV-digested DNA from uncloned WR virus, vA41L and vA41L-rev gave fragments of 1991bp that were detected with a probe extending from the 5' region of the gene into the left flanking sequences and by a probe from near the 3' end of the gene within the region deleted from vΔA41L. As expected, this 3' probe did not detect any fragment in vΔA41L and the 5' probe detected a smaller fragment of 1391 bp, consistent with the loss of the majority of the A41L ORF. PCR analysis using oligonucleotides flanking the ORF detected fragments of indistinguishable size in WR, vA41L and vA41L-rev viruses and a fragment 600 nucleotides smaller for vΔA41L (data not shown).

The growth of vA41L, vΔA41L and vA41L-rev viruses were equivalent in cell culture. The plaques formed on BS-C-1 cells by each virus were the same size and the yields of intracellular virus produced 24 h postinfection (hpi) of BS-C-1 cells at 1 pfu/cell was indistinguishable for each virus (data not shown).

Expression and purification of the A41L protein

To demonstrate expression of the A41L protein from baculovirus, proteins in the supernatants of AcA41Lhis-infected Sf21 cells were analysed by immunoblotting with a monoclonal antibody against the His(6) tag (Clontech) (FIG. 4a). This antibody detected a 30 kDa protein made by AcA41Lhis but not by AcNPV confirming that the A41L protein was expressed and secreted from baculovirus-infected cells.

The A41Lhis protein was purified from baculovirus-infected Sf21 cell supernatants by nickel affinity chromatography (FIG. 4b). A41Lhis was detected as the predominant protein in cell supernatants by staining with Coomassie blue. The A41Lhis protein was removed selectively by passage of the clarified supernatant through the nickel column. The bound A41Lhis protein was eluted from the column in increasing concentrations of imidazole with the majority of A41Lhis protein eluting in 60 mM imidazole. The eluted protein was further purified by anion exchange chromatography using a mono-Q column and FPLC. The purified protein obtained appeared homogeneous (data not shown) and was used for immunisation of rabbits and for BIAcore 2000 surface plasmon resonance analysis as described in Materials and Methods.

The A41L protein is secreted from VV-infected cells

Figure 4:
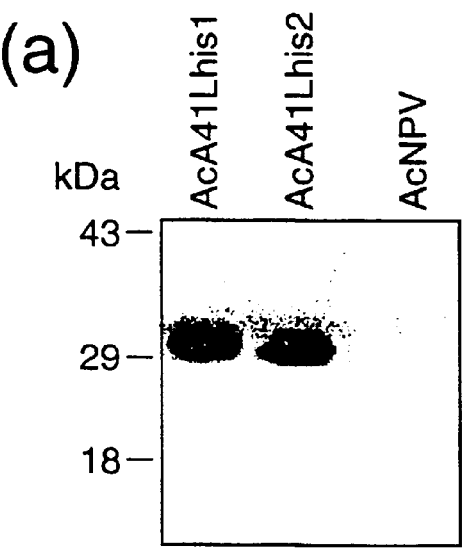
FIG. 4 shows the presence of recombinant A41L protein in supernatants from cells infected with baculovirus expressing A41L.
Figure 4:
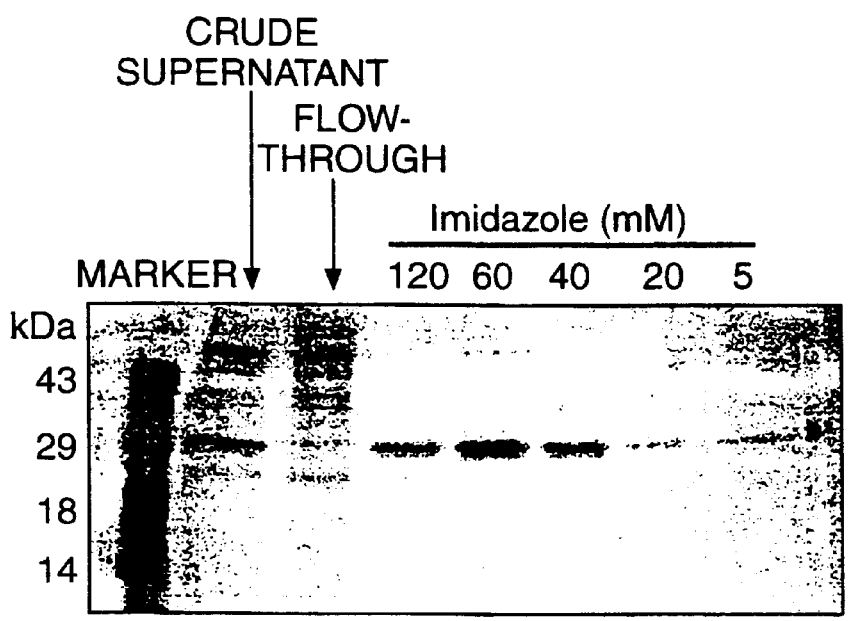

To identify and characterise the VV A41L protein an antibody was produced by immunisation of rabbits with the purified A41Lhis protein and used in immunoblotting to detect the A41L protein made from VV-infected cells (FIG. 4). A 30 kDa protein was detected in the supernatant of cells infected with WR, vA41L, and vA41L-rev but not vΔA41L (FIG. 5a). To determine when during infection the protein was produced, supernatants were taken at different times postinfection or after infection in the presence of cytosine arabinoside (araC), an inhibitor of virus DNA replication and therefore of intermediate and late protein synthesis (FIG. 5b). The A41L protein was detected as early as 2 hpi and in the presence of araC, indicating that it was expressed early. However, the protein was also expressed late during infection as the levels continued to increase up to 16 hpi. This early and late expression parallels that of vCKBP which is expressed from the early/late p7.5 promoter that has been widely used in poxvirus expression vectors (Smith, 1991). The A41L protein had a decreased size when synthesised in the presence of either tunicamycin or monensin and therefore contains both N and O-linked carbohydrate (FIG. 5c).

The A41L protein is conserved in orthopoxviruses

Figure 6:
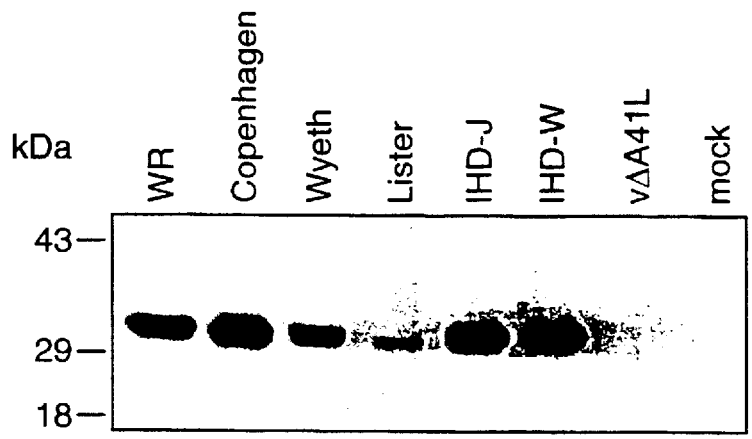
FIG. 6 shows the presence of proteins recognised by anti-A41L antibody in supernatants of cells infected by various poxviruses.
Figure 6:
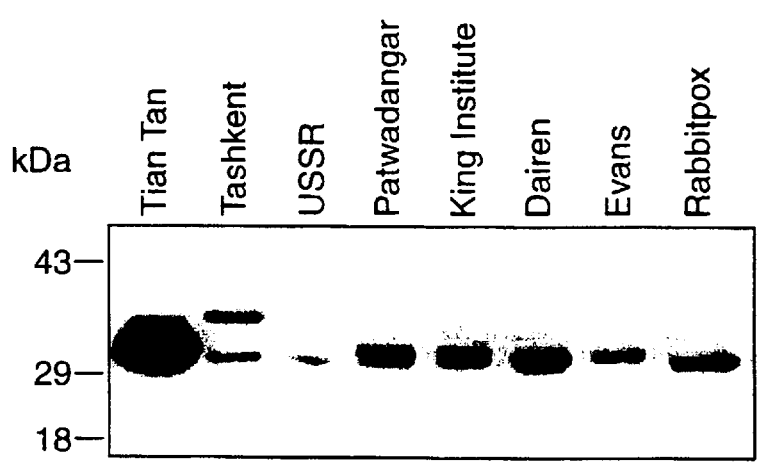
Figure 6:
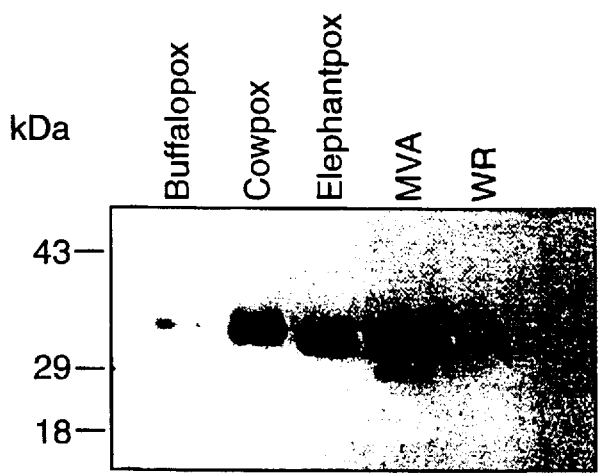

The DNA sequence data on orthopoxvirus genomes indicated that the A41L gene is highly conserved. This was examined further by immunoblotting with supernatants from cells infected with 16 strains of VV and 2 strains of cowpox virus (FIG. 6). The data show that all these viruses express a protein of similar size, but at variable levels, that is recognised by the anti-A41L antibody.

The A41L protein binds CXC chemokines Mig and IP-10

Figure 7A:
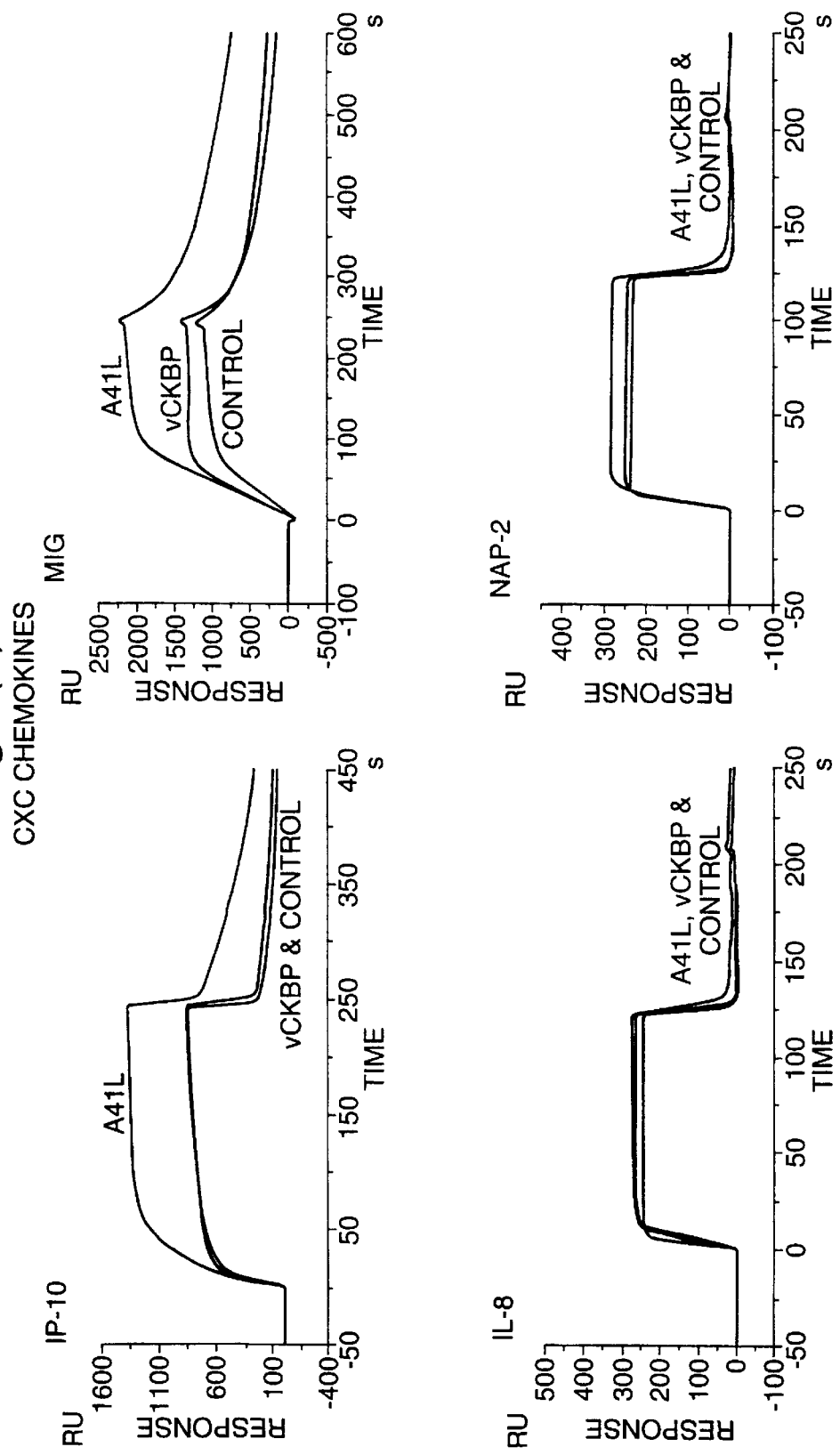
FIG. 7 shows binding profiles for A41L and vCKBP with a variety of chemokines.

The similarity of the A41L protein to vCKBP suggested that, like vCKBP, it might bind chemokines. However, supernatants from VV WR-infected cells were shown not to contain a protein that bound the human CC chemokines MiP-1α or RANTES, or the human CXC chemokines GRO-α and IL-8. To determine if the A41L protein bound to other chemokines that were not included in that study, the purified A41Lhis and 35Khis (vCKBP) proteins were chemically cross-linked via EDC onto an NHS-activated carboxymethylated cellulose CM5 biosensor chip in separate flow cells of the BIAcore 2000 system (Pharmacia). The chip surface was then deactivated using ethanolamine hydrochloride to remove unbound proteins. Various recombinant human chemoattractant proteins (including 6 CC chemokines, 8 CXC chemokines, the C chemokine lymphotactin and the complement C5a anaphylatoxin) were sequentially passed across the chip surface in all flow cells. Hydrochloric acid (0.1 M) was used to regenerate the chip surface after each chemoattractant protein was passed across. As expected the CC chemokines MIP-1α and MCP-1 gave positive signals with vCKBP compared to A41L or control (FIG. 7b) confirming they were bound by vCKBP but not by A41L. With the CXC chemokines IL-8 and NAP-2 no specific binding was observed to either vCKBP or A41L, but both Mig and IP-10 bound specifically to A41L (FIG. 7a). All other chemokines tested NAP-2, GRO-α, GRO-γ, PF4, SDF-1α, ENA-78, RANTES, MCP-2, eotaxin, I-309, lymphotactin, and the anaphylatoxin C5a were not bound by A41L (data not shown).

The A41L protein inhibits infiltration of cells into infected rabbit skin

To determine if the A41L protein could influence the host response to infection with VV, viruses vA41L, vΔA41L and vA41L-rev ($10^4$ pfu) injected subcutaneously into rabbit skin and the lesions examined 3 days later. There were distinct differences in cellular infiltration and viral antigen between lesions induced by the virus (vΔA41L) not expressing A41L and those expressing A41L (vA41L and vA41L-rev). Immunostaining of lesions infected with vΔA41L using anti-rabbit CD43 antibody, revealed intense infiltration of CD43+cells (stained reddish brown), in the lower vascular regions of the skin, as compared to that of vA41L and vA41L-rev, which exhibited few infiltrating cells. The amount of VV antigen present in the dermis and epidermis, as revealed by immunostaining with the anti-14k monoclonal antibody, was more extensive (stained reddish brown) in lesions caused by vA41L and vA41L-rev than that of vΔA41L. This demonstrates that the A41L protein could down-modulate the infiltration of monocytes, macrophages and T lymphocytes during an anti-viral immune response in vivo (presumably by binding and inhibiting IP-10 and Mig), and thus enable greater viral dissemination through the skin lesion. This contrasts with the vΔA41L virus, which displayed reduced viral spread when confronted with immune infiltration.

Discussion

Here we present a characterisation of the protein encoded by VV gene A41L. This gene product is a secreted glycoprotein of 30 kDa that is expressed by all 18 strains of orthopoxvirus tested and the gene is also highly conserved in three strains of variola virus. Despite its conservation the protein is not required for VV replication and spread in cell culture. Nonetheless the A41L protein binds to the CXC chemokines Mig and IP-10 but not to 15 other CC and CXC chemokines. In this respect it displays a much greater chemokine selectivity than the recently identified vCKBP, with which it shares structural similarity, that binds promiscuously to all CC chemokines tested (Alcami et al., 1998). Hereafter the A41L protein is called vCKBP-2, the 35 kDa protein of VV strain Lister being termed vCKBP-1.

IP-10 and Mig represent a sub-group of the CXC chemokines, for review see (Farber, 1997). They are more closely related to each other (37% amino acid identity) than to other CXC chemokines and their expression by keratinocytes, endothelial cells, lymphocytes, monocytes and neutrophils is induced by IFN-γ(Luster & Ravetch, 1987b; Luster & Ravetch, 1987a; Farber, 1993; Cassatella et al., 1997). IP-10 and Mig also differ from other CXC chemokines in that they do not attract neutrophils but instead stimulate migration of monocytes and activated T lymphocytes (Taub et al., 1993). The genes encoding IP-10 and Mig are close together on chromosome 4 at a locus distinct from the cluster of other CXC chemokine genes (Lee & Farber, 1996). Both IP-10 and Mig are bound by a seven transmembrane G-protein-coupled receptor (CXCR3) that exhibits greater selectivity than some other CKRs and specifically recognises IP-10 and Mig, but not other CXC and CC chemokines (Loetscher et al., 1996). CXCR3 also shows selectivity in that it is expressed on T cells only after their activation (Loetscher et al., 1996). This specific expression suggests a selective IFN-γ-dependent recruitment or infiltration of effector T lymphocytes by Mig and IP-10. These chemokines have been implicated in the recruitment of such cells in delayed-type hypersensitivity (DTH) cutaneous lesions in tuberculoid leprosy (Kaplan et al., 1987), in cutaneous Leishmaniasis (Kaplan et al., 1987) and in autoimmune inflammatory diseases such as psoriasis (Gottlieb et al., 1988; Gottlieb, 1990), in which high IP-10 expression levels were detected. Mig and IP-10 are implicated in the recruitment of activated T cells following virus or protozoal infection (Amichay et al., 1996; Asensio & Campbell, 1997; Cheret etal., 1997; Narumi etal., 1997) and in some situations can contribute to pathology e.g. in chronic infection with hepatitis C virus (Narumi et al., 1997). Other conditions in which IP-10 may play a causative role in disease are in adult respiratory distress syndrome, (Abdullah etal., 1997), Lyme disease (Ebnet etal., 1996), atherosclerosis and restenosis (Wang et al., 1996), breast cancer cell migration, invasion and metastasis (Youngs et al., 1997), cutaneous T cell lymphomas (Sarris et al., 1996) and tubulointerstitial nephritis associated with glomerular disease (Tang et al., 1997). IP-10 and Mig also suppress production of haemopoietic progenitor cells (Schwartz et al., 1997) which might be disadvantageous following bone marrow transplants.

As a soluble and selective inhibitor of Mig and IP-10, vCKBP-2 represents a novel compound that has pharmaceutical importance as a selective reagent to inhibit excessive inflammatory reactions and tissue damage induced by these chemokines. It may be possible to prevent or ameliorate disease induced by these chemokines by administration of vCKBP-2 or molecules derived from it. In addition a study of the structural interactions of vCKBP-2 complexed with Mig and IP-10 may provide valuable information about the interactions of these chemokines with the cellular receptor CXCR3. This information would aid the design of small inhibitors to block the interaction of Mig and IP-10 with CXCR3. Presently it is not easy to achieve these goals by manipulation of CXCR3 because of its membrane association and lack of soluble derivative molecules that retain chemokine-binding activity.

The specificity of vCKBP-2 is interesting with regard to the biology of VV and other orthopoxviruses expressing this protein. Several orthopoxviruses also express a protein (vCKBP-1) that binds CC chemokines and therefore restricts the recruitment of monocytes and other cells attracted by CC chemokines, such as eosinophils by eotaxin (Graham et al., 1997; Smith et al., 1997a; Alcami et al., 1998). However, they do not express a CXC chemokine-binding protein (other than vCKBP-2 which is Mig and IP-10 specific) that would inhibit recruitment of neutrophils. This might suggest that the recruitment of activated T cells, monocytes and macrophages is more important for control and clearance of VV infection than the recruitment of neutrophils. Alternatively it is possible that VV has another mechanism to block the normal function of neutrophils.

Here we show that vCKBP-2 influences profoundly the recruitment of inflammatory cells to sites of VV infection in rabbit skin and the degree of virus replication and spread as shown by the amount of virus antigen. This is consistent with the observations that VV infection does induce Mig and IP-10 expression (Amichay et al., 1996) and that expression of Mig and IP-10 from recombinant VV caused a decrease in VV virulence (Ramshaw et al., 1997). The removal of the A41L gene is also likely to increase the immunogenicity and safety of VV strains such as VV MVA, a safe and immunogenic VV strain that is being developed as a recombinant therapeutic vaccine against various cancers and a range of pathogens, including for instance, malaria, human papilloma virus (HPV) and human immunodeficiency virus (HIV).

In summary we have identified a novel protein expressed by poxviruses that binds to the CXC chemokines Mig and IP-10 and will therefore interfere with the host response to infection. This molecule, called vCKBP-2, has therapeutic potential as an inhibitor of conditions induced by excessive Mig and IP-10 activity, and of infections induced by pathogens binding to CXCR3. It may be a useful reagent for the detection of these chemokines in kits and the manipulation of the encoding gene may enable the construction of more immunogenic poxvirus based vaccines.

References

Abdullah, F., Ovadia, P., Feuerstein, G., Neville, L. F., Morrison, R., Mathiak, G., Whiteford, M., and Rabinovici, R. (1997). The novel chemokine mob-1: involvement in adult respiratory distress syndrome. Surgery 122, 303–312.

Aguado, B., Selmes, I. P., and Smith, G. L. (1992). Nucleotide sequence of 21.8 kbp of variola major virus strain Harvey and comparison with vaccinia virus. J. Gen. Virol. 73, 2887–2902.

Alcami, A., and Smith, G. L. (1992). A soluble receptor for interleukin-1β encoded by vaccinia virus: a novel mechanism of virus modulation of the host response to infection. Cell 71, 153–167.

Alcami, A., and Smith, G. L. (1995a). Cytokine receptors encoded by poxviruses: a lesson in cytokine biology. Immunol. Today 16, 474–478.

Alcami, A., and Smith, G. L. (1995b). Vaccinia, cowpox, and camelpox viruses encode soluble gamma interferon receptors with novel broad species specificity. J Virol 69, 4633–9.

Alcami, A., Symons, J. A., Collins, P. D., Williams, T. J., and Smith, G. L. (1998). Blockade of chemokine activity by a soluble chemokine-binding protein from vaccinia virus. J. Immunol. 160, 624–633.

Amichay, D., Gazzinelli, R. T., Karupiah, G., Moench, T. R., Sher, A., and Farber, J. M. (1996). Genes for chemokines MuMig and Crg-2 are induced in protozoan and viral infections in response to IFN-gamma with patterns of tissue expression that suggest nonredundant roles in vivo. J. Immunol. 157, 4511–4520.

Asensio, V. C., and Campbell, I. L. (1997). Chemokine gene expression in the brains of mice with lymphocytic choriomeningitis. J. Virol. 71, 7832–7840.

Baggiolini, M., Dewald, B., and Moser, B. (1997). Human chemokines: an update. Annu. Rev. Immunol. 15, 675–705.

Boyle, D. B., and Coupar, B. E. H. (1988). A dominant selectable marker for the construction of recombinant poxviruses. Gene 65, 123–128.

Cassatella, M. A., Gasperini, S., Calzetti, F., Bertagnin, A., Luster, A. D., and McDonald, P. P. (1997). Regulated production of the interferon-gamma-inducible protein-10 (IP-10) chemokine by human neutrophils. Eur. J. Immunol. 27, 111–115.

Cheret, A., Le Grand, R., Caufour, P., Neildez, O., Matheux, F., Theodoro, F., Boussin, F., Vaslin, B., and Dormont, D. (1997). Chemoattractant factors (IP-10, MIP-1alpha, IL-16) mRNA expression in mononuclear cells from different tissues during acute SIVmac251 infection of macaques. J. Med. Primatol. 26,19–26.

Cook, D. N., Beck, M. A., Coffman, T. M., Kirby, S. L., Sheridan, J. F., Pragnell, I. B., and Smithies, 0. (1995). Requirement of MIP-1α for an inflammatory response to viral infection. Science 269,1583–1585.

Czerny, C. P., and Mahnel, H. (1990). Structural and functional analysis of orthopoxvirus epitopes with neutralizing monoclonal antibodies. J. Gen. Virol. 71, 2341–2352.

D'Souza, M. P., and Harden, V. A. (1996). Chemokines and HIV-1second receptors. Nature Medicine 2, 1293–1300.

Devereux, J., Haeberli, P., and Smithies, O. (1984). A comprehensive set of sequence analysis programs for the VAX. Nucl. Acids. Res. 12, 387–395.

Ebnet, K., Simon, M. M., and Shaw, S. (1996). Regulation of chemokine gene expression in human endothelial cells by proinflammatory cytokines and Borrelia burgdorferi. Ann. N. Y. Acad. Sci. 797, 107–117.

Esposito, J. R., Condit, R. C., and Obijeski, J. (1981). The preparation of orthopoxvirus DNA. J. Virol. Meth. 2, 175–179.

Falkner, F. G., and Moss, B. (1988). Escherichia coli gpt gene provides dominant selection for vaccinia virus open reading frame expression vectors. J. Virol. 62, 1849–1854.

Falkner, F. G., and Moss, B. (1990). Transient dominant selection of recombinant vaccinia viruses. J. Virol. 64, 3108–3111.

Farber, J. M. (1993). HuMIG: A new human member of the chemokine family of cytokines. Biochem. Biophys. Res. Com. 192, 223–230.

Farber, J. M. (1997). Mig and IP-10: CXC chemokines that target lymphocytes. J. Leukoc. Biol. 61, 246–57.

Fauci, A. S. (1996). Host factors and the pathogenesis of HIV-induced disease. Nature 384, 529–534.

Fenner, F., Anderson, D. A., Arita, I., Jezek, Z., and Ladnyi, I. D. (1988). "Smallpox and Its Eradication." World Health Organisation, Geneva.

Goebel, S. J., Johnson, G. P., Perkus, M. E., Davis, S. W., Winslow, J. P., and Paoletti, E. (1990). The complete DNA sequence of vaccinia virus. Virology 179, 247–266.

Gottlieb, A. B. (1990). Immunologic mechanisms in psoriasis. J. Invest. Dermatol. 95, 18S–19S.

Gottlieb, A. B., Luster, A. D., Posnett, D. N., and Carter, D. M. (1988). Detection of a gamma interferon-induced protein IP-10 in psoriatic plaques. J. Exp. Med. 168, 941–948.

Graham, K. A., Lalani, A. S., Macen, J. L., Ness, T. L., Barry, M., Liu, L., Lucas, A., Clark-Lewis, I., Moyer, R. W., and McFadden, G. (1997). The T1/35kDa family of poxvirus-secreted proteins bind chemokines and modulate leukocyte influx into virus-infected tissues. Virology 229,12–24.

Howard, 0. M., Ben-Baruch, A., and Oppenheim, J. J. (1996). Chemokines: progress toward identifying molecular targets for therapeutic agents. *Trends Biotechnol.* 14, 46–51.

Howard, S. T., Chan, Y. S., and Smith, G. L. (1991). Vaccinia virus homologues of the Shope fibroma virus inverted terminal repeat proteins and a discontinuous ORF related to the tumor necrosis factor receptor family. *Virology* 180, 633–647.

Hughes, S. J., Johnston, L. H., de Carlos, A., and Smith, G. L. (1991). Vaccinia virus encodes an active thymidylate kinase that complements a cdc8 mutant of *Saccharomyces cerevisiae*. *J. Biol. Chem.* 266, 20103–20109.

Johnson, G. P., Goebel, S. J., and Paoletti, E. (1993). An update on the vaccinia virus genome. *Virology* 196, 381–401.

Kaplan, G., Luster, A. D., Hancock, G., and Cohn, Z. A. (1987). The expression of a gamma interferon-induced protein (IP-10) in delayed immune responses in human skin. *J. Exp. Med.* 166, 1098–1108.

Kerr, S. M., and Smith, G. L. (1991). Vaccinia virus DNA ligase is nonessential for virus replication: recovery of plasmids from virus-infected cells. *Virology* 180, 625–632.

Laemmi, U. K. (1970). Cleavage of structural proteins during the assembly of the head of bacteriophage T4. *Nature* 227, 680–685.

Lalani, A. S., Graham, K., Mossman, K., Rajarathnam, K., Clark-Lewis, I., Kelvin, D., and McFadden, G. (1997). The purified myxoma virus gamma interferon receptor homolog M-T7 interacts with the heparin-binding domains of chemokines. *J. Virol.* 71, 4356–4363.

Lee, H. H., and Farber, J. M. (1996). Localization of the gene for the human MIG cytokine on chromosome 4q21 adjacent to INP10 reveals a chemokine "mini-cluster". *Cytogenet. Cell Genet.* 74, 255–258.

Loetscher, M., Gerber, B., Loetscher, P., Jones, S. A., Piali, L., Clark-Lewis, I., Baggiolini, M., and Moser, B. (1996). Chemokine receptor specific for IP10 and MIG: structure, function, and expression in activated T-lymphocytes. *J. Exp. Med.* 184, 963–969.

Luster, A. D., and Ravetch, J. V. (1987a). Biochemical characterization of a gamma interferon-inducible cytokine (IP-10). *J. Exp. Med.* 166, 1084–1097.

Luster, A. D., and Ravetch, J. V. (1987b). Genomic characterization of a gamma-interferon-inducible gene (IP-10) and identification of an interferon-inducible hypersensitive site. *Mol. Cell. Biol.* 7, 3723–3731.

Mackett, M., and Smith, G. L. (1982). Vaccinia virus: a selectable eukaryotic cloning and expression vector. *Proc. Natl. Acad. Sci. USA* 79, 7415–7419.

Mackett, M., Smith, G. L., and Moss, B. (1985). The construction and characterization of vaccinia virus recombinants expressing foreign genes. In "DNA Cloning: A Practical Approach." (D. M. Glover, Ed.), Vol. 2, pp. 191–211. IRL Press, Oxford.

Martinez-Pomares, L., Thompson, J. P., and Moyer, R. W. (1995). Mapping and investigation of the role in pathogenesis of the major unique secreted 35-kDa protein of rabbitpox virus. *Virology* 206, 591–600.

Massung, R. F., Liu, L., Qi, J., Knight, J. C., Yuran, T. E., Kerlavage, A. R., Parsons, J. M., Venter, J. C., and Esposito, J. J. (1994). Analysis of the complete genome of smallpox variola major virus strain Bangladesh-1975. *Virology* 201, 215–240.

McFadden, G., Graham, K., Ellison, K., Barry, M., Macen, J., Schreiber, M., Mossman, K., Nash, P., Lalani, A., and Everett, H. (1995). Interruption of cytokine networks by poxviruses: lessons from myxoma virus. *J. Leukocyte Biol.* 57, 731–738.

Moss, B. (1991). Vaccinia virus: a tool for research and vaccine development. *Science* 252, 1662–1667.

Moss, B. (1996). Poxviridae: the viruses and their replication. In "*Fields Virology*" (B. N. Fields, D. M. Knipe, and P. M. Howley, Eds.), pp. 2637–2671. 2 vols. Lippincott Raven Press, N. Y.

Mossman, K., Nation, P., Macen, J., Garbutt, M., Lucas, A., and McFadden, G. (1996). Myxoma virus M-T7, a secreted homolog of the interferon-gamma receptor, is a critical virulence factor for the development of myxomatosis in European rabbits. *Virology* 215, 17–30.

Murphy, P. M. (1996). Chemokine receptors: structure, function and role in microbial pathogenesis. *Cyt. Growth Fact. Revs.* 7, 47–64.

Narumi, S., Tominaga, Y., Tamaru, M., Shimai, S., Okumura, H., Nishioji, K., Itoh, Y., and Okanoue, T. (1997). Expression of IFN-inducible protein-10 in chronic hepatitis. *J. Immunol.* 158, 5536–5544.

Parkinson, J. E., and Smith, G. L. (1994). Vaccinia virus gene A36R encodes a $M_r$ 43–50 K protein on the surface of extracellular enveloped virus. *Virology* 204, 376–390.

Patel, A. H., Gaffney, D. F., Subak-Sharpe, J. H., and Stow, N. D. (1990). DNA sequence of the gene encoding a major secreted protein of vaccinia virus, strain Lister. *J. Gen. Virol.* 71, 2013–2021.

Premack, B. A., and Schall, T. J. (1996). Chemokine receptors: gateways to inflammation and infection. *Nature Medicine* 2, 1174–1178.

Ramshaw, I. A., Ramsay, A. J., Karupiah, G., Rolph, M. S., Mahalingam, S., and Ruby, J. C. (1997). Cytokines and immunity to viral infections. *Immunol. Revs.* 159, 119–135.

Rose-John, S., and Heinrich, P. C. (1994). Soluble receptors for cytokines and growth factors: generation and biological function. *Biochem. J.* 300, 281–290.

Sarris, A. H., Daliani, D., Ulmer, R., Crow, M., Broxmeyer, H. E., Pugh, W., Reiss, M., Cabanillas, F., Deisseroth, A. B., and Duvic, M. (1996). Interferon-inducible protein-10 and the pathogenesis of cutaneous T-cell lymphomas. *Leuk. Lymphoma* 24, 103–110.

Schwartz, G. N., Liao, F., Gress, R. E., and Farber, J. M. (1997). Suppressive effects of recombinant human monokine induced by IFN-gamma (rHuMig) chemokine on the number of committed and primitive hemopoietic progenitors in liquid cultures of CD34+ human bone marrow cells. *J. Immunol.* 159, 895–904.

Sekido, N., Mukaida, N., Harada, A., Nakanishi, I., Watanabe, Y., and Matsushima, K. (1993). Prevention of lung reperfusion injury in rabbits by a monoclonal antibody against interleukin-8. *Nature* 365, 654–657.

Shchelkunov, S. N. (1995). Functional organization of variola major and vaccinia virus genomes. *Virus Genes* 10, 53–71.

Shchelkunov, S. N., Blinov, V. M., Resenchuk, S. M., Totmenin, A. V., Olenina, L. V., Chirikova, G. B., and Sandakhchiev, L. S. (1994). Analysis of the nucleotide sequence of 53 kbp from the right terminus of the genome of variola virus strain India-1967. *Virus Res.* 34, 207–236.

Smith, C. A., Smith, T. D., Smolak, P. J., Friend, D., Hagen, H., Gerhart, M., Park, L., Pickup, D. J., Torrance, D., Mohler, K., Schooley, K., and Goodwin, R. G. (1997a). Poxvirus genomes encode a secreted, soluble protein that preferentially inhibits β chemokine activity yet lacks sequence homology to known chemokine receptors. *Virology* 236, 316–327.

Smith, G. L. (1991). Vaccinia virus vectors for gene expression. *Curr. Opin. Biotechnol.* 2, 713–717.

Smith, G. L. (1996). Virus proteins that bind cytokines, chemokines or interferons. *Curr. Opin. Immunol.* 8, 467–471.

Smith, G. L., Alcami, A., and Symons, J. A. (1997b). Poxvirus chemokine-binding protein, British Patent Application number 9703592.7.

Smith, G. L., Chan, Y. S., and Howard, S. T. (1991). Nucleotide sequence of 42 kbp of vaccinia virus strain WR from near the right inverted terminal repeat. *J. Gen. Virol.* 72, 1349–1376.

Smith, G. L., Symons, J. A., Khanna, A., Vanderplasschen, A., and Alcami, A. (1997c). Vaccinia virus immune evasion. *Immunol. Revs.* 159, 137–154.

Southern, E. (1975). Detection of specific DNA sequences among DNA fragments separated by gel electrophoresis. *J. Mol. Biol.* 98, 503–517.

Spriggs, M. K. (1996). One step ahead of the game: viral immunomodulatory molecules. *Annu. Rev. Immunol.* 14, 101–130.

Tang, W. W., Qi, M., Warren, J. S., and Van, G. Y. (1997). Chemokine expression in experimental tubulointerstitial nephritis. *J. Immunol.* 159, 870–876.

Taub, D. D., Lloyd, A. R., Conlon, K., Wang, J. M., Ortaido, J. R., Harada, A., Matsushima, K., Kelvin, D. J., and Oppenheim, J. J. (1993). Recombinant human interferon-inducible protein 10 is a chemoattractant for human monocytes and T lymphocytes and promotes T cell adhesion to endothelial cells. *J. Exp. Med.* 177, 1809–1814.

Towbin, H., Staehelin, T., and Gordon, J. (1979). Electrophoretic transfer of proteins from polyacrylamide gels to nitrocellulose sheets: procedure and some applications. *Proc. Natl. Acad. Sci. USA*. 76, 4350–4354.

Upton, C., DeLange, A. M., and McFadden, G. (1987). Tumorigenic poxviruses: genomic organisation and DNA sequence of the telomeric region of the Shope fibroma virus genome. *Virology* 160, 20–30.

Upton, C., Mossman, K., and McFadden, G. (1992). Encoding of a homolog of the IFN-gamma receptor by myxoma virus. *Science* 258, 1369–1372.

Wang, X., Yue, T. L., Ohistein, E. H., Sung, C. P., and Feuerstein, G. Z. (1996). Interferon-inducible protein-10 involves vascular smooth muscle cell migration, proliferation, and inflammatory response. *J. Biol. Chem.* 271, 24286–93.

Youngs, S. J., Ali, S. A., Taub, D. D., and Rees, R. C. (1997). Chemokines induce migrational responses in human breast carcinoma cell lines. *Int. J. Cancer* 71, 257–266.

Figure legends

FIG. 1. Alignment of the amino acid sequences of the VV WR A41L protein (Smith et al., 1991), vCKBP from VV Lister (Patel et al., 1990) created using the PILEUP and PRETTYPLOT programmes of the Genetics Computer Group Inc. Wisconsin (Devereux et al., 1984). Amino acids in boxes are conserved between both proteins. The 8 conserved cysteine resides after the N-terminal siganl peptide are marked with a dot.

FIG. 2. Hydrophobicity plots of VV WR A41L (Smith et al., 1991) and vCKBP proteins (Patel et al., 1990) created with the GCG package (Devereux et al., 1984). The regions between the pairs of vertical lines of vCKBP represent regions absent from the A41L protein.

FIG. 3. Southern blot analysis of recombinant virus genomes. (a) Diagram showing the predicted structures of the virus genomes, the sizes of the EcoRV fragment spanning the A41L gene for the different viruses and the positions of the two probes used for Southern blotting. (b) Southern blot. Virus DNA was digested with restriction endonuclease EcoRV, run on a 0.8% agarose gel, transferred to nylon filters and probed with fluorescein-labelled DNA probes derived from the regions indicated in (a). Bound probes were detected as described in the Materials and Methods. The sizes of the bands in nucleotides that were detected with the two probes are indicated.

FIG. 4. Expression and purification of the A41L protein. (a) Immunoblot. Proteins in the supernatants of AcA41Lhis (clones 1 and 2)-infected Sf21 cells were resolved by SDS-PAGE (10% gel), transferred to nitrocellulose and probed with a rabbit antiserum directed against the A41L protein. (b) Commassie stained gel showing the purification of the A41Lhis protein by nickel-chelate affinity chromatography. Proteins present in the crude supernatant are compared to proteins present in the flowthrough after application to the nickel column and to proteins eluting in increasing concentrations of imidazole. The sizes of protein molecular mass markers are shown in kDa.

Figure 5:
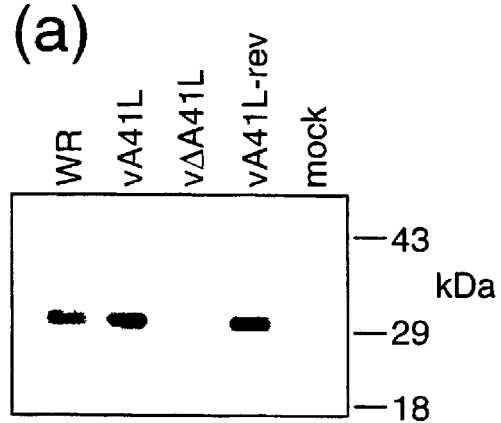
FIG. 5 shows the presence of A41L in supernatants of virus-infected cells.
Figure 5:
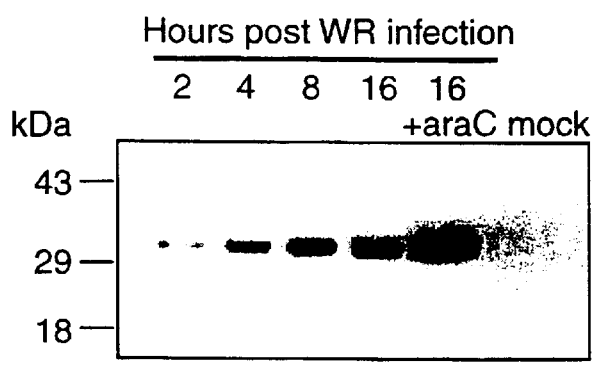
Figure 5:
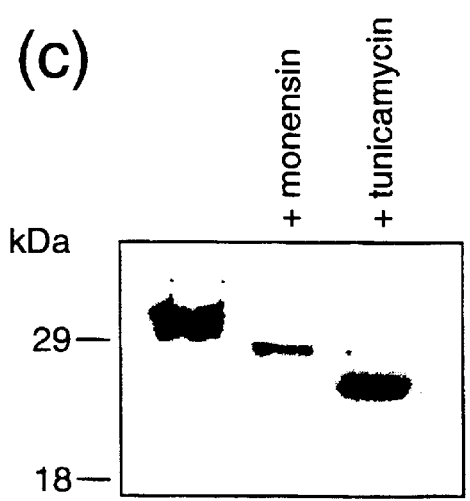

FIG. 5. Immunoblots showing a characterisation of the A41L protein made by VV WR. (a) BS-C-1cells were infected with the indicated viruses at 10 pfu/cell or mock-infected and supernatants prepared 16 hpi. After separation by SDS-PAGE (10% gel) and transfer to nitrocellulose, the blots were incubated with rabbit antiserum raised against the A41L protein and bound antibody detected as described in Materials and Methods. (b) The A41L protein is made early and late during infection. Cells were infected with WR virus for the indicated length of time or infected in the presence of 40 μg/ml of araC or mock-infected. Supernatants were prepared and analysed as in (a). (c) The A41L protein contains N- and O-linked carbohydrate. Cells were infected with WR virus in the presence or absence of monensin (1 μM) or tunicamycin (1 μg/ml) for 16 h. Supernatants were prepared and analysed as in (a).The sizes of protein molecular mass markers are indicated in kDa.

FIG. 6. The A41L protein is conserved in orthopoxviruses. BS-C-1 cells were infected with the indicated viruses or mock-infected and supernatants were prepared 16 hpi as described in Materials and Methods. Proteins were analysed by SDS-PAGE (10% gel), transferred to nitrocellulose and probed with the rabbit antiserum against the A41L protein. Bound antibody was detected as described in Materials and Methods. The sizes of protein molecular mass markers are indicated in kDa.

FIG. 7. BIAcore 2000 analysis. Purified A41Lhis or vCKBP proteins were immobilised in separate flow cells and the binding of the indicated chemokines analysed as described in Materials and Methods. Control represents a third flow cell in which no protein was coupled to the chip surface. a) CXC chemokines. b) CC chemokines. Sensorgrams are shown.

FIG. 8. The nucleotide sequence of the VV strain WR A41L gene and flanking sequences (Smith et al., 1991). The coding region of the A41L gene starts at position 121 and finishes at position 780.

What is claimed is:

1. A recombinant poxvirus which is genetically engineered to be incapable of expressing a native A41L protein.

2. The recombinant poxvirus according to claim 1, which is incapable of expressing a chemokine-binding A41L protein.

3. The recombinant poxvirus according to claim 1, which is a genetically engineered vaccina virus.

* * * * *

SEQUENCE LISTING

<160> NUMBER OF SEQ ID NOS: 1

<210> SEQ ID NO 1
<211> LENGTH: 897
<212> TYPE: DNA
<213> ORGANISM: Vaccinia virus

<400> SEQUENCE: 1

```
aaacttgaca ttagcatttt attcttatta caaaatataa aataaaatat acaatccaat        60
actcacataa tccaactcac tcgaacacta tttttccaat tacgataaca atattgcaga       120
atgtactcgt tagtatttgt tattttgatg tgtataccat ttagttttca aacagtgtat       180
gatgataaat cggtatgcga ttctgacaat aaagaatata tgggaataga agtttatgta       240
gaagcaacgc tagacgaacc cctcagacaa acaacgtgtg aatccaaaat ccataaaatt       300
ggtgcatctg tatcaaacgg aggattaaat atttctgttg atctattaaa ctgtttttctt      360
aattttcata cagttggtgt atacactaat cgcgataccg tatacgcgaa gtttgctagt       420
ttggatccat ggactacgga acctataaat tctatgaccc atgacgatct agtaaaatta       480
acagaagaat gtatagtgga catttattta aaatgtgaag tggataaaac aaaggatttc       540
atgaaaacta acggtaatag attaaaacca agagacttta aaactgttcc tccttctaat       600
gtaggaagca tgatagaact acagtctgac tattgcgtaa acgatgtgac tacatacgtc       660
aaaatatacg atgagtgtgg aaacattaaa cagcattcca ttccaacact aagagattat       720
tttaccacca agaatggtca accacgtaaa atattaaaga aaaaatttga taattgttaa       780
ttgttatttt tataaaaaca agaacggtac ggcgatattt attttttttct aaaacatcta     840
accgaagtag tggtatgata aaaatgtagt gtaattgtta tatagtgtaa cacgaat          897
```